United States Patent [19]

Johnson

[11] Patent Number: 5,149,268

[45] Date of Patent: Sep. 22, 1992

[54] METHOD OF FILLING AN ENDODONTICALLY PREPARED ROOT CANAL

[76] Inventor: William B. Johnson, 5010 E. 68th St., Suite 104, Tulsa, Okla. 74136

[21] Appl. No.: 696,753

[22] Filed: Apr. 16, 1991

[51] Int. Cl.$^5$ ................................................ A61C 5/02
[52] U.S. Cl. .................................................... 433/224
[58] Field of Search .................... 433/224, 226, 81, 75

[56] References Cited

U.S. PATENT DOCUMENTS

| | | | |
|---|---|---|---|
| 3,318,000 | 5/1967 | Paris | 433/224 |
| 3,534,476 | 10/1970 | Winters | 433/224 |
| 3,813,779 | 6/1974 | Tosti | 433/224 |
| 3,919,774 | 11/1975 | Fishman | 433/224 |
| 4,758,156 | 7/1988 | Johnson | 433/81 |
| 4,986,754 | 1/1991 | Chang et al. | 433/228.1 |

FOREIGN PATENT DOCUMENTS 1220369  4/1987  Canada .............................. 433/224

*Primary Examiner*—Cary E. O'Connor
*Attorney, Agent, or Firm*—Head and Johnson

[57] ABSTRACT

A method is provided for filling an endodontically prepared root canal in a tooth including the steps of injecting flowable filler material, such as gutta percha, preferably after the filler material has been heated, into the root canal to at least substantially fill the root canal, inserting an obturator shaft into the root canal to displace the flowable filler material to more completely fill the root canal, and severing the obturator shaft into two portions, retaining the shaft portion therein within the root canal and removing the severed portion from the tooth. The root canal having been filled, the tooth can then be repaired in the normal procedure for completion of an endodontic procedure.

3 Claims, 2 Drawing Sheets

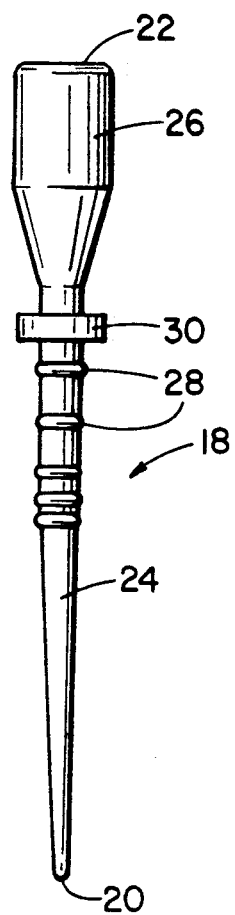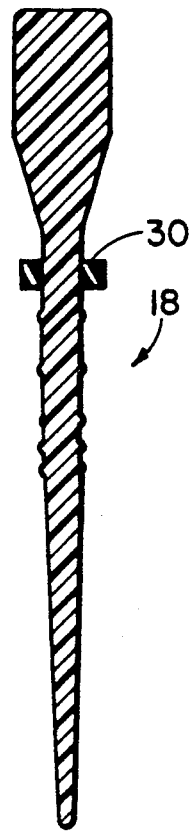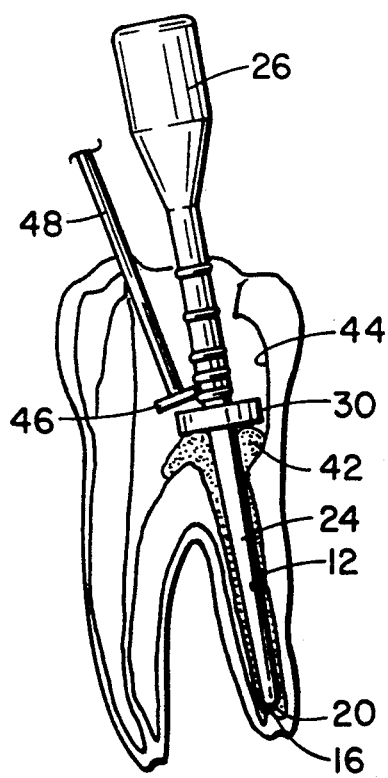
Fig. 6
Fig. 7
Fig. 8

METHOD OF FILLING AN ENDODONTICALLY PREPARED ROOT CANAL

BACKGROUND OF THE INVENTION

Conventional techniques for preforming endodontic therapy on teeth are time consuming. Further, such procedures do not always adequately ensure that the entire canal system is filled with the repair material. Experience has shown that it is not possible to remove all pulpal remanents and contaminants from a root canal with current preparation techniques. If the pulpal remanents and contaminants are thoroughly entombed in the repair material, the endodontic therapy can be successful. If the remanents and contaminants are not thoroughly entombed, there is a high probability of failure of the therapy.

To achieve a high degree of success in endodontic therapy complete obturation of the canal system is necessary. Experience has shown that failure to completely obturate the canal system is the primary cause of failure in endodontic therapy. In the past, the usual means of filling an endodontically prepared root canal is by the use of a condenser, that is, a manually held tool having a small diameter shaft, usually flat on the end. The technician, whether a dentist or an endodontic specialist, applies filler material by dipping the condenser into a quantity of filler material, such as gutta percha, and inserting it into the root canal repeatedly to fill the canal, the condenser being used to compact the filler material in the root canal. This procedure is exceedingly time consuming, and the results are not uniformly predictable. Such system can fail to completely obturate the root canal.

Others have provided more automated systems in which the filler material is placed in a cylinder in a hand-held gun-like machine. The filler material is heated and by pressure to the filler material within the cylinder, the filler material is forced through a small tubular needle directly into the root canal. This procedure is advantageous over the purely manual condenser technique and has the significant advantage of reducing the time required to fill the root canal. However, any system that depends entirely upon compaction of filler material within a root canal is subject to some degree of failure because of the nature of filler material in current use, and particularly of the nature of gutta percha, the most commonly used filler material.

Gutta percha is frequently heated prior to use increase the plasticity thereof. When placed in a tooth it cools fairly quickly and when it cools is not subject to free flow into lateral passageways that might exist in the root canal that needs to be obturated in order to have a completely successful procedure.

The present invention relates to an improved method of filling the root canal in which filler material is applied by a filler gun thorough a tubular needle directly into the root canal in a tooth, followed by the insertion of the shaft portion of an obturator appliance into the root canal. The insertion of a physical device into a root canal filled with filler material tends to compact and disperse the filler material into all areas in the root canal, and particularly into lateral passageways, in a manner that is superior to other hereto known systems.

SUMMARY OF THE INVENTION

The method of filling an endodontically prepared root canal of this invention includes a sequence of steps. After a root canal has been thoroughly cleaned of all pulpal material and contaminants to the extent practically possible, the canal must be filled or obturated so as to prevent the entrance of foreign matter and body fluids therein and to ensure a successful endodontic procedure. After the root canal has been treated endodontically in the normal way and is ready to be filled the practitioner, according to the principles of this invention, employs the use of an obturator appliance. The obturator appliance is in the form of a manually employed element having an elongated, usually tapered shaft portion with a distal end and having, at the proximal end, an enlarged diameter handle portion. The obturator is of dimensions such that when inserted into an endodontically prepared root canal, the distal end will extend at least substantially to the root canal apex. The appliance typically has depth markings on the elongated shaft in the area between the portion that is receivable in a root canal and the handle portion.

The practitioner inserts the shaft portion of the appliance into the root canal so that the distal end thereof reaches to, or at least substantially to, the root canal apex. The practitioner notices, such as by use of depth markings, the depth of the obturator shaft in the root canal. The obturator is then removed from the tooth.

Next, the practitioner inserts filler material into the root canal to at least substantially fill the root canal. This can be accomplished by inserting the filler material utilizing a condenser tool or by insertion of flowable filler material through an application tip inserted into the root canal.

After the root canal is filled with filler material the shaft portion of the appliance is inserted into the root canal to displace and more completely compact the filler material and to force filler material into areas of the root canal that may not have been fully filled utilizing the initial filling procedure.

As the shaft portion of the appliance is inserted into the root canal the practitioner observes the depth of insertion of the shaft portion and continues to insert the appliance shaft portion while observing the depth until the full depth is achieved as previously noted to indicate that the appliance distal end is at or substantially at the root canal apex.

Next, the practitioner severs the appliance shaft into two portions. This can be accomplished utilizing a rotating burr. The appliance shaft is severed above the shaft portion extending within the root canal so as to separate substantially all of the appliance except the shaft portion extending within the root canal, including the portion thereof having the handle portion. The practitioner then removes the severed portion from the tooth, leaving the shaft portion of the appliance within the root canal to serve as a portion of the canal filling material.

Thereafter, the endodontic procedure is completed as in the usual manner that generally includes filling the cavity formed in the tooth to gain access to the root canal.

A better understanding of the invention will be obtained by reference to the attached description of the preferred embodiment which is taken in conjunction with the attached drawings.

DESCRIPTION OF THE DRAWINGS

FIG. 6 is an external elevational enlarged view of an obturator appliance that is used in practicing the method of this invention.

FIG. 7 is a cross-sectional view of the obturator appliance of FIG. 6.

FIG. 8 shows the shaft portion of the obturator appliance inserted into the canal to compact and radially displace the filler material therein with the obturator distal end at the canal apex. FIG. 8 shows the use of a burr for severing the obturator appliance into two portions, one of the portions having the shaft received in the canal that is retained within the tooth and the portion having the handle portion being removed from the tooth. In a preferred method of practicing the invention, the obturator appliance of FIG. 6 is inserted into the tooth of FIG. 1 to enable the practitioner to notice the depth thereof so that the depth of the obturator as obtained in FIG. 8 can be verified. Alternatively, a severable obturator, such as illustrated and described in U.S. Pat. No. 4,894,011 may be employed.

DESCRIPTION OF THE PREFERRED EMBODIMENT

Figure 1:
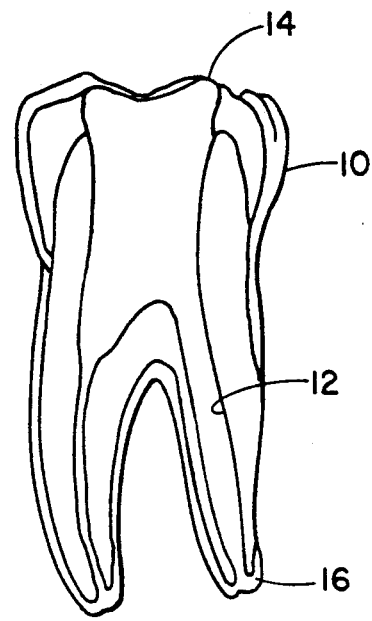
FIG. 1 is a cross-sectional view of a typical tooth showing a root canal that has been endodontically prepared to be filled with a filler material as in the part of a typical endodontic procedure.

Referring first to FIG. 1, a tooth of a general type, indicated by the numeral 10, has a root canal 12 therein. The root canal 12 extends from an area below the tooth crown 14 to the root apex 16. In performing an endodontic procedure the practitioner, usually an endodontist or a denist, thoroughly cleans root canal 12 of all pulpal and other contaminant material. This is usually achieved by small diameter files having rough exterior surfaces that are inserted into root canal 12 and reciprocated to loosen the pulpal material. This procedure is repeated until the pulpal material has been removed as thoroughly as practically possible from root canal 12.

In order to achieve a successful endodontic procedure, root canal 12 must be thoroughly sealed, and for this purpose a filler material is employed. The most commonly used filler material at the present time is gutta percha, a naturally occurring plastic-like substance that can be heated to cause it to form phases and that has proven to be a successful material for filling root canals.

FIGS. 6 and 7 show an obturator appliance, indicated generally by the numeral 18, that is used in practicing the methods of this invention. The obturator appliance 18 is of the type such as shown in U.S. Pat. Nos. 4,758,156 and 4,894,011 and described in great detail in patent application Ser. No. 07/640,047. The teachings of U.S. Pat. Nos. 4,758,156; 4,894,011 and the subject matter of U.S. patent application Ser. No. 07/640,047 are incorporated herein by reference. Generally speaking the obturator appliance 18 is a body having a distal end 20 and a proximal end 22. A slender shaft portion 24 preferably tapered, as shown, extends to distal end 20. At the proximal end 22 is an enlarged diameter handle portion 26 that is of increased size to make manual manipulation of the obturator appliance easier.

The upper part of shaft portion 24 includes length markers 28 that serve to indicate the length of the shaft from distal end 20. Instead of being referred to as "length markers" markers 28 may also be termed "depth markers."

The obturator appliance 18 may be made of metal or preferably of plastic and is preferably unitary.

Positioned on the upper end of shaft portion 24 is a rubber washer 30 that can be used to help compact the filler material in a root canal.

In a preferred method of practicing the invention, the first step in filling root canal 12 of the tooth of FIG. 1, after it has been endodontically prepared, is to insert shaft portion 24 of obturator appliance 18 into root canal 12 so that distal end 20 is at or substantially at the root canal apex 16. The practitioner then observes and mentally notes the depth of shaft portion 24 in the root canal, which can be observed by noting the position of depth markers 28.

The obturator appliance 18 is then removed. The purpose of inserting the obturator into the root canal initially is to establish the position of the obturator in the root canal when it has been inserted to the depth so that distal end 20 is at or substantially at the apex of the root canal.

Figure 2:
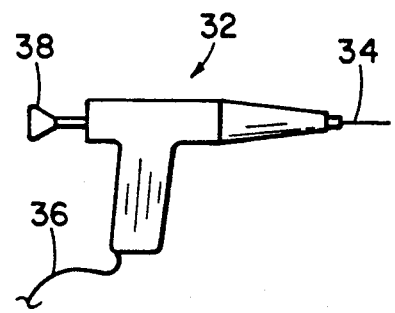
FIG. 2 is a diagrammatic elevational view of a typical applicator for use in inserting filler material into an endodontically prepared root canal. The applicator having an applicator needle through which the filler material is forced into the canal.

Next, the root canal is filled with filler material. This can be accomplished in a variety of ways. In one method an application tool that has a general appearance as illustrated in FIG. 2 is utilized, the application tool being generally indicated by the numeral 32. The application tool 32 is a commercially available product such as manufactured by Texceed and sold under the trademark OBTURA II. It is understood that the use of such a tool is not indispensable in the practicing of this invention but is illustrated as one method. The applicator tool 32 has a tubular needle 34 that is of small diameter. The applicator 32 has therein a reservoir for the placement of a quantity of filler material, such as a cylinder, having communication with needle 34. Means is provided within applicator tool 32 to heat the filler material, such as energy supplied by flexible cable 36. A plunger 38, when manually depressed, moves the heated filler material through needle 34 to fill a root canal.

Figure 3:
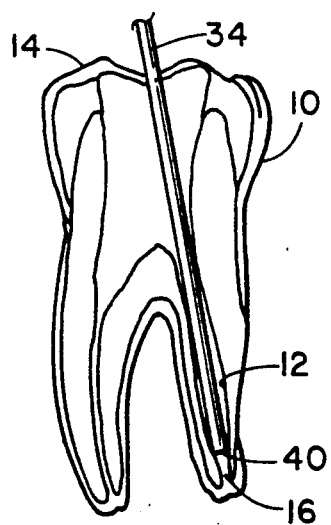
FIG. 3 shows the needle portion of an applicator inserted into the root canal to near the apex of the canal at which point the filling procedure begins.

FIG. 3 shows needle 34, such as from an applicator tool 32, extended within root canal 12 with the tip end 40 of needle 34 adjacent the root canal apex 16.

Figure 4:
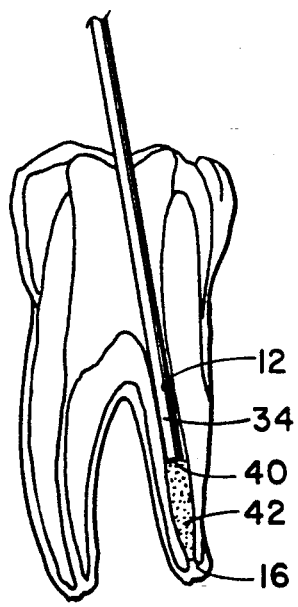
FIG. 4 shows the applicator tip in the root canal raised above the apex and with filler material from the applicator tip inserted into the root canal.

Filler material is injected through needle 34 to fill the root canal. The filler material being indicated in FIG. 4 by the numeral 42. As the root canal is filled needle 34 is withdrawn.

Figure 5:
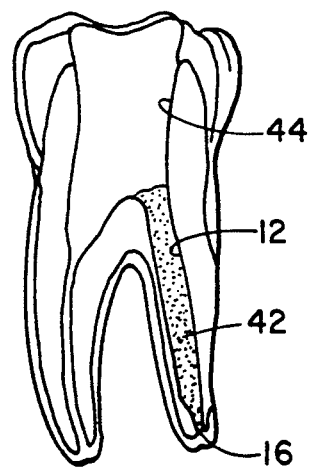
FIG. 5 shows the tooth of FIG. 1 with the endodontically prepared root canal substantially filled with filler material.

FIG. 5 shows the tooth of FIG. 1 with root canal 12 filled with filler material 42. While, as previously indicated, the use of an applicator tool 32 as shown in FIG. 2 is an example of a method of filling a root canal, any method that substantially fills root canal 12 with filler material serves the purpose of this invention. The root canal 12, as in Fig. 5, should be filled with filler material utilizing the best procedure available to the practitioner at the time.

The procedure to the point of FIG. 5 is frequently employed and to complete the endodontic procedure, cavity 44 formed in the tooth to provide access to the root canal 12 is filled.

The procedure described to this point functions satisfactorily in many instances. The purpose of this invention is to provide a way to improve the effectiveness of filling root canal 12 that carries the usual filling procedure further.

For this purpose, after the root canal has been filled as effectively as possible with filler material to the state as indicated in FIG. 5, shaft portion 24 of obturator appliance 18 is inserted into the filled root canal 12. The shaft portion serves to displace and compact filler material 42. This compaction serves to more completely fill the root canal, and this is particularly true with reference to any radially extending passageways in the tooth structure or other irregular features of the root canal. The insertion of the obturator appliance 18 serves particularly to radially compact the filler material that is difficult to achieve utilizing normal filling procedures, such as that previously described and such as accomplished utilizing an applicator of the type identified by the numeral 32. Further, the obturator serves to reduce shrinkage of the filler material.

Prior to the insertion of the obturator appliance 18, the practitioner will normally move the sliding stopper 30 down onto shaft 24 so that as the shaft is inserted into the filled root canal, the displaced filler material 42 serves to slide stopper 30 upwardly. Thus, the stopper helps maintain the filler material in the root canal to more securely fill the root canal.

In order to obtain maximum effectiveness of the use of the obturator appliance 18, it is important that the apical end 20 thereof be positioned at, or as near possible to, the root canal apex 16, that is, it is desirable that the obturator appliance distal end 20 be positioned at or adjacent to the root canal apex 16. The practitioner can know that such is accomplished by observing the depth of the shaft portion within the root canal to conform to the depth indication previously obtained when the shaft was inserted into the root canal before any filler material was inserted therein. Thus, the use of the depth indicator or markers 28 is important in successfully practicing the method of this disclosure.

After shaft portion 24 is inserted to the depth required, obturator appliance 18 is severed into two portions. This is illustrated in FIG. 8 and can be accomplished utilizing a dental burr 46 rotated by a shaft 48. After severance of the proximal portion, including handle portion 26, the portion shaft 24 above the severed point is removed from the tooth. In addition, sliding stopper 30 is removed. The portion of the obturator shaft 24 below the point of severance is retained within the tooth, and the retained portion of shaft 24 serves as an integral part of the filler material utilized to obturate root canal 12. Thus, the root canal is filled with a two-component system, that is, a flowable filler material 42, such as gutta percha, and a physical obturator in the form of a retained shaft portion 24.

The endodontic procedure can then be completed in the ussual way by filling the cavity 44, encapsulating the filler material 42 and the retained portion of the obturator shaft 22 in the tooth.

The procedure described herein results in increased effectiveness of filling root canals. The procedure which employs the use of the obturator appliance 18 can be practiced in a way that it does not substantially increase the time required for the practitioner to complete an endodontic procedure and yet in a manner which substantially increases the effectiveness of an obturator procedure.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of filling an endodontically prepared root canal in a tooth employing an obturator in the form of an elongated slender body having a proximal end and a distal end, the obturator body having a handle portion at said proximal end, the body having a shaft portion from the handle portion to said distal end, such shaft portion being dimensioned so that the portion thereof adjacent said distal end may be received in the endodontically prepared root canal, the obturator body having a plurality of integral spaced apart length indicators formed on the exterior surface of the shaft portion between the handle portion and the portion adjacent the distal end to be received in the endodontically prepared root canal, the indicators serving to indicate the length of the shaft portion to the distal end, comprising the steps of:

(a) inserting the shaft portion of an obturator body into the root canal so that the shaft portion distal end at least substantially reaches the root canal apical end;
   (b) noting the depth of the obturator body shaft portion in the root canal using the depth indicators;
   (c) withdrawing the obturator body from the root canal;
   (d) inserting filler material into the root canal to at least substantially fill the root canal;
   (e) inserting the obturator body shaft portion into the root canal to displace the filler material to more completely fill the root canal;
   (f) observing the depth of insertion of the shaft portion of the obturator body and continuing to insert the obturator body shaft portion while observing the depth until the full depth is achieved as noted in step (b); and
   (g) severing the obturator body handle portion from the obturator body shaft portion;
   (h) retaining the shaft portion thereof with the root canal; and
   (i) removing the severed handle portion from the tooth.

2. A method of filling an endodontically prepared root canal according to claim 1 wherein said step (d) of injecting filler material into said root canal includes injecting heated filler material, the heating serving to increase the plasticity of the filler material.

3. A method of filling an endodontically prepared root canal according to claim 1 wherein said step (g) of severing said obturator body handle portion from the obturator body shaft portion includes severing said obturator shaft with a rotating cut off burr.

* * * * *